US012640271B2

(12) United States Patent
McCarthy et al.

(10) Patent No.: US 12,640,271 B2
(45) Date of Patent: May 26, 2026

(54) INTERACTABLE AND INTERPRETABLE TEMPORAL DISEASE RISK PROFILES

(71) Applicant: Optum Services (Ireland) Limited, Dublin (IE)

(72) Inventors: Michael J. McCarthy, Dublin (IE); Kieran O'Donoghue, Dublin (IE); Neill Michael Byrne, Dublin (IE)

(73) Assignee: OPTUM SERVICES (IRELAND) LIMITED, Dublin (IE)

( * ) Notice: Subject to any disclaimer, the term of this patent is extended or adjusted under 35 U.S.C. 154(b) by 354 days.

(21) Appl. No.: 17/469,005

(22) Filed: Sep. 8, 2021

(65) Prior Publication Data
US 2023/0075176 A1     Mar. 9, 2023

(51) Int. Cl.
*G16H 50/30*     (2018.01)
*G06F 3/0481*     (2022.01)
(Continued)

(52) U.S. Cl.
CPC ............. *G16H 50/30* (2018.01); *G16H 10/60* (2018.01); *G16H 50/20* (2018.01); *G06F 3/0481* (2013.01); *G06F 16/22* (2019.01)

(58) Field of Classification Search
CPC ........ G16H 50/20; G16H 50/70; G16H 10/60; G16H 50/30; G06F 16/22; G06F 3/0481
See application file for complete search history.

(56) References Cited

U.S. PATENT DOCUMENTS

| | | |
|---|---|---|
| 6,788,965 B2 | 9/2004 | Ruchti et al. |
| 8,036,925 B2 | 10/2011 | Choubey |

(Continued)

FOREIGN PATENT DOCUMENTS

| | | |
|---|---|---|
| CN | 112185569 A | 1/2021 |
| CN | 113241135 A | 8/2021 |

(Continued)

OTHER PUBLICATIONS

Choi et al, RETAIN: An Interpretable Predictive Model for Healthcare using Reverse Time Attention Mechanism, 2016, Advances in Neural Information Processing Systems, pp. 3512-3520 (Year: 2016).*

(Continued)

*Primary Examiner* — Gregory Lultschik
(74) *Attorney, Agent, or Firm* — Alston & Bird LLP

(57)     ABSTRACT

Various embodiments provide methods, apparatus, systems, computing entities, and/or the like, providing a temporal disease risk profile describing a likelihood of disease onset over time for an individual in a dynamically interpretable manner. Interpretability of the temporal disease risk profile is enabled by providing additional and contextual information, such as weight distributions of various health indicators, factors, and features. In an embodiment, an example method comprises generating a temporal disease risk profile comprising risk score nodes based at least in part on providing a plurality of record data objects to a risk scoring machine learning model configured to generate a risk score; providing the temporal disease risk profile for display via a first user interface comprising a plurality of interactable node mechanisms each corresponding to a risk score node; and providing a node-specific weight distribution comprising one or more sub-nodal weight values for display via a second user interface.

12 Claims, 10 Drawing Sheets

(51) Int. Cl.

| | | |
|---|---|---|
| G16H 10/60 | (2018.01) | |
| G16H 50/20 | (2018.01) | |
| G06F 16/22 | (2019.01) | |

(56) References Cited

U.S. PATENT DOCUMENTS

| | | | |
|---|---|---|---|
| 8,321,251 B2 | 11/2012 | Opalach et al. | |
| 8,751,266 B2 | 6/2014 | Stang | |
| 9,147,041 B2 | 9/2015 | Amarasingham et al. | |
| 9,324,119 B2 | 4/2016 | Singh et al. | |
| 9,836,599 B2 | 12/2017 | Sheldon et al. | |
| 10,231,622 B2 | 3/2019 | Soyao et al. | |
| 10,249,389 B2 | 4/2019 | Athey et al. | |
| 10,404,526 B2 | 9/2019 | Prabhakara et al. | |
| 10,496,788 B2 | 12/2019 | Amarasingham et al. | |
| 10,579,928 B2 | 3/2020 | Wang et al. | |
| 10,692,589 B2 | 6/2020 | Mueller-Wolf | |
| 10,729,502 B1 | 8/2020 | Wolf et al. | |
| 10,888,281 B2 | 1/2021 | Shah et al. | |
| 10,943,072 B1 | 3/2021 | Jaganmohan | |
| 11,065,079 B2 | 7/2021 | Wolf et al. | |
| 11,081,234 B2 | 8/2021 | Pappada | |
| 11,106,442 B1 | 8/2021 | Hsiao et al. | |
| 11,116,587 B2 | 9/2021 | Wolf et al. | |
| 11,562,294 B2 | 1/2023 | Seo et al. | |
| 11,941,531 B1 | 3/2024 | Arik et al. | |
| 2003/0060692 A1 | 3/2003 | Ruchti et al. | |
| 2005/0091084 A1* | 4/2005 | McGuigan | G16H 50/30 705/3 |
| 2006/0206359 A1 | 9/2006 | Stang | |
| 2008/0214904 A1* | 9/2008 | Saeed | A61B 5/0006 705/2 |
| 2009/0182594 A1 | 7/2009 | Choubey | |
| 2011/0071363 A1 | 3/2011 | Montijo et al. | |
| 2013/0035976 A1 | 2/2013 | Buffett | |
| 2013/0110576 A1 | 5/2013 | Roy et al. | |
| 2013/0172764 A1* | 7/2013 | Buckley | A61B 5/4842 600/509 |
| 2013/0185097 A1 | 7/2013 | Saria et al. | |
| 2014/0074509 A1 | 3/2014 | Amarasingham et al. | |
| 2014/0279641 A1 | 9/2014 | Singh et al. | |
| 2015/0213206 A1 | 7/2015 | Amarasingham et al. | |
| 2015/0213224 A1 | 7/2015 | Amarasingham et al. | |
| 2015/0216413 A1 | 8/2015 | Soyao et al. | |
| 2015/0286792 A1* | 10/2015 | Gardner | G16H 50/30 705/3 |
| 2015/0289821 A1 | 10/2015 | Rack-Gomer et al. | |
| 2016/0267268 A1 | 9/2016 | Sheldon et al. | |
| 2017/0061093 A1 | 3/2017 | Amarasingham et al. | |
| 2017/0091320 A1 | 3/2017 | Psota et al. | |
| 2017/0111245 A1 | 4/2017 | Ishakian et al. | |
| 2017/0124269 A1 | 5/2017 | McNair et al. | |
| 2017/0357771 A1 | 12/2017 | Connolly et al. | |
| 2018/0083825 A1 | 3/2018 | Prabhakara et al. | |
| 2018/0211727 A1 | 7/2018 | Zarkoob et al. | |
| 2018/0225314 A1 | 8/2018 | Devarao et al. | |
| 2018/0330824 A1 | 11/2018 | Athey et al. | |
| 2018/0374580 A1 | 12/2018 | Gupta et al. | |
| 2019/0034590 A1 | 1/2019 | Oren et al. | |
| 2019/0034591 A1 | 1/2019 | Mossin et al. | |
| 2019/0036970 A1* | 1/2019 | Shih | G06F 21/6245 726/26 |
| 2019/0108912 A1 | 4/2019 | Spurlock, III et al. | |
| 2019/0147343 A1 | 5/2019 | Lev et al. | |
| 2019/0172587 A1* | 6/2019 | Park | G16H 50/30 705/2 |
| 2019/0377818 A1 | 12/2019 | Andritsos | |
| 2020/0019840 A1 | 1/2020 | Guo et al. | |
| 2020/0043612 A1 | 2/2020 | McNair et al. | |
| 2020/0074573 A1 | 3/2020 | Op Den Buijs et al. | |
| 2020/0160995 A1* | 5/2020 | Kenig | G16H 50/20 |
| 2020/0185085 A1 | 6/2020 | Mavrieudus et al. | |
| 2020/0236402 A1 | 7/2020 | Spanias et al. | |
| 2020/0272919 A1 | 8/2020 | Haimson et al. | |
| 2020/0293527 A1 | 9/2020 | Srivastav et al. | |
| 2020/0356846 A1 | 11/2020 | Saripalli et al. | |
| 2020/0396231 A1 | 12/2020 | Krebs et al. | |
| 2020/0411176 A1 | 12/2020 | Hadorn et al. | |
| 2021/0082575 A1* | 3/2021 | Ji | G16H 40/20 |
| 2021/0090733 A1 | 3/2021 | Dibari et al. | |
| 2021/0142199 A1 | 5/2021 | Mccarthy et al. | |
| 2021/0201184 A1 | 7/2021 | Scheepens et al. | |
| 2021/0241137 A1* | 8/2021 | Jain | G06N 5/04 706/11 |
| 2021/0279644 A1 | 9/2021 | Givental et al. | |
| 2021/0286815 A1 | 9/2021 | Aylett et al. | |
| 2021/0302953 A1 | 9/2021 | Zhou et al. | |
| 2021/0390668 A1 | 12/2021 | Ren et al. | |
| 2022/0051796 A1 | 2/2022 | Zhu et al. | |
| 2022/0103589 A1 | 3/2022 | Shen et al. | |
| 2022/0291966 A1 | 9/2022 | Masood et al. | |
| 2022/0292339 A1 | 9/2022 | Byrne et al. | |
| 2022/0327404 A1* | 10/2022 | Godden | G06N 5/04 706/12 |
| 2023/0024366 A1* | 1/2023 | Krutka | G16H 10/60 |
| 2023/0061808 A1 | 3/2023 | Nicholas | |
| 2023/0104028 A1 | 4/2023 | Wang et al. | |
| 2023/0119186 A1 | 4/2023 | O'Donoghue et al. | |
| 2023/0122121 A1 | 4/2023 | O'Donoghue et al. | |
| 2023/0140828 A1 | 5/2023 | Durvasula et al. | |
| 2023/0376532 A1 | 11/2023 | Mccarthy et al. | |
| 2024/0028907 A1 | 1/2024 | Shi et al. | |
| 2024/0119057 A1 | 4/2024 | Unsal et al. | |
| 2024/0207485 A1 | 6/2024 | Tran et al. | |
| 2024/0211779 A1 | 6/2024 | Conchuir et al. | |
| 2024/0273263 A1 | 8/2024 | James et al. | |
| 2024/0355460 A1 | 10/2024 | Sobolewski et al. | |
| 2024/0362068 A1 | 10/2024 | O Conchuir et al. | |
| 2024/0378385 A1 | 11/2024 | Byrne et al. | |
| 2024/0378516 A1 | 11/2024 | Waldron et al. | |
| 2024/0379160 A1 | 11/2024 | Harari et al. | |
| 2024/0403628 A1 | 12/2024 | O Conchuir et al. | |

FOREIGN PATENT DOCUMENTS

| | | |
|---|---|---|
| EP | 3767636 A1 | 1/2021 |
| WO | 2019/201997 A1 | 10/2019 |
| WO | 2021/115835 A1 | 6/2021 |

OTHER PUBLICATIONS

Hardt et al, Explaining an increase in predicted risk for clinical alerts, 2020, CHIL '20: Proceedings of the ACM Conference on Health, Inference, and Learning, pp. 80-89 (Year: 2020).*

Gao et al, StageNet: Stage-Aware Neural Networks for Health Risk Prediction, 2020, WWW '20: Proceedings of The Web Conference 2020, pp. 530-540 (Year: 2020).*

Darabi, Sajad et al. "TAPER: Time-Aware Patient EHR Representation," IEEE Journal of Biomedical and Health Informatics, vol. 24, Issue 11, pp. 3268-3275, Apr. 3, 2020 (ePub: Nov. 2020), DOI: 10.1109/JBHI.2020.2984931.

International Search Report and Written Opinion for International Application No. PCT/US2023/018975, dated Aug. 7, 2023, (15 pages), European Patent Office, Rijswijk, Netherlands.

Sarwar, Tabinda et al. "The Secondary Use Of Electronic Health Records For Data Mining: Data Characteristics and Challenges," ACM Computing Surveys, vol. 55, No. 2, Article 33, pp. 33:1-33:40, Jan. 18, 2022, DOI: 10.1145/3490234.

Jacobi, Corinna et al. "Coming To Terms With Risk Factors For Eating Disorders—Application Of Risk Terminology and Suggestions For A General Taxonomy," Psychological Bulletin, vol. 130, No. 1, (2004), pp. 19-65, DOI: 10.1037/0033.2909.130.1.19.

Wenke, Sam et al. "Contextual Recurrent Neural Networks," arXiv Preprint arXiv:1902.03455v1 [cs.LG] Feb. 9, 2019, (7 pages).

Assale, Michela et al. "The Revival of The Notes Field: Leveraging The Unstructured Content In Electronic Health Records," Frontiers In Medicine, vol. 6, Article 66, Apr. 17, 2019, pp. 1-23, DOI: 10.3389/fmed.2019.00066.

Bayramli, Ilkin et al. "Predictive Structured-Unstructured Interactions In EHR Models: A Case Study of Suicide Prediction," Nature

(56)             References Cited

OTHER PUBLICATIONS

Partner Journals|Digital Medicine, vol. 5, No. 15, Jan. 27, 2022, pp. 1-11, DOI: 10.1038/s41746-022-00558-0.

Camargo, Manuel et al. "Discovering Generative Models From Event Logs: Data-Driven Simulation vs Deep Learning," arXiv preprint arXiv:2009.03567v1 [cs.AI], Sep. 8, 2020, (12 pages).

Miotto, Riccardo et al. "Deep Patient: An Unsupervised Representation To Predict The Future of Patients From The Electronic Health Records," Scientific Reports, vol. 6, No. 26094, May 17, 2016, pp. 1-10, DOI: 10.10.8/srep26094.

Mogren, Olof. "C-RNN-GAN: Continuous Recurrent Neural Networks With Adversarial Training," arXiv preprint arXiv:1611.09904 [cs.AI], Nov. 29, 2016, (6 pages).

Nolle, Timo et al. "DeepAlign: Alignment-Based Process Anomaly Correction Using Recurrent Neural Networks," In: Dustdar S., Yu E., Salinesi C., Rieu D., Pant V. (eds) Advanced Information Systems Engineering. CAiSE 2020. Lecture Notes in Computer Science, vol. 12127, pp. 319-333, Springer, Cham. DOI: 10.1007/978-3-030-49435-3_20.

Syring, Anja F. et al. "Evaluating Conformance Measures In Process Mining Using Conformance Propositions," In book: Transactions on Petri Nets and Other Models of Concurrency XIV, Nov. 21, 2019, pp. 192-221, Springer, Berlin, Heidelberg. DOI: 10.1007/978-3-662-60651-3_8.

Tello-Leal Edgar et al. "Predicting Activities in Business with LSTM Recurrent Neural Networks," In 2018 ITU Kaleidoscope: Machine Learning for a 5G Future (ITU K), Nov. 26, 2018, (7 pages). IEEE. DOI: 10.23919/ITU-WT.2018.8598069.

Theis, Julian et al. "Adversarial System Variant Approximation To Quantify Process Model Generalization," IEEE Access, vol. 8, Oct. 23, 2020, pp. 194410-194427. DOI: 10.1109/ACCESS.2020.3033450.

Zhang, Dongdong et al. "Combining Structured and Unstructured Data For Predictive Models: A Deep Learning Approach," BMC Medical Informatics and Decision Making, vol. 20, No. 280, Oct. 29, 2020, pp. 1-11, DOI: 10.1186/s12911-020-01297-6.

Non-Final Rejection Mailed on May 23, 2024 for U.S. Appl. No. 17/663,771, 42 page(s).

Non-Final Rejection Mailed on Aug. 27, 2024 for U.S. Appl. No. 17/196,543, 34 page(s).

Basiri et al, "ABCDM: An Attention-based Bidirectional CNN-RNN Deep Model for Sentiment Analysis", Future Generation Computer Systems, vol. 115, Feb. 2021, pp. 279-294 (Year: 2021).

Behera, et al., "Generative Adversarial Networks Based Remaining useful Life Estimation for IIoT," Computers & Electrical Engineering 92 (2021): 107195. (Year: 2021).

Dangut, et al., "Rare Failure Prediction using an Integrated Autoencoder and Bidirectional Gated Recurrent Unit Network." IFAC—PapersOnLine 53.3 (2020): 276-282. (Year: 2020).

Daras et al., "Your Local GAN: Designing Two Dimensional Local Attention Mechanisms for Generative Models", Proceedings of the IEEE/CVF Conference on Computer Vision and Pattern Recognition (CVPR), 2020, pp. 14531-14539 (Year: 2020).

Elsheikh, et al, "Bidirectional Handshaking LSTM for Remaining useful Life Prediction," Neurocomputing 323 (2019): 148-156. (Year: 2019).

Final Rejection Mailed on Jan. 15, 2025 for U.S. Appl. No. 17/196,543, 28 page(s).

Liu et al, "DSTP-RNN: A Dual-stage Two-phase Attention-based Recurrent Neural Network for Long-term and Multivariate Time Series Prediction", Expert Systems with Applications, vol. 143, Apr. 1, 2020, 113082 (Year: 2020).

Notice of Allowance and Fees Due (PTOL-85) Mailed on Feb. 4, 2025 for U.S. Appl. No. 17/451,270, 20 page(s).

Notice of Allowance and Fees Due (PTOL-85) Mailed on Feb. 7, 2025 for U.S. Appl. No. 17/504,657, 8 page(s).

Notice of Allowance and Fees Due (PTOL-85) Mailed on Feb. 12, 2025 for U.S. Appl. No. 17/451,270, 2 page(s).

Notice of Allowance and Fees Due (PTOL-85) Mailed on Feb. 13, 2025 for U.S. Appl. No. 17/504,657, 3 page(s).

Notice of Allowance and Fees Due (PTOL-85) Mailed on Jan. 14, 2025 for U.S. Appl. No. 17/663,771, 9 page(s).

Sarwar, et al. "The Secondary use of Electronic Health Records for Data Mining: Data Characteristics and Challenges", ACM Com. Surv., 55 (2) (2023), p. 33 (Year: 2023).

Notice of Allowance and Fees Due (PTOL-85) Mailed on Sep. 25, 2024 for U.S. Appl. No. 17/663,771, 12 page(s).

Advisory Action (PTOL-303) Mailed on Apr. 1, 2025 for U.S. Appl. No. 17/196,543, 2 page(s).

Notice of Allowance and Fees Due (PTOL-85) Mailed on May 14, 2025 for U.S. Appl. No. 17/504,657, 3 page(s).

Non-Final Rejection Mailed on Jul. 28, 2025 for U.S. Appl. No. 17/196,543, 29 page(s).

Final Rejection Mailed on Feb. 27, 2026 for U.S. Appl. No. 17/196,543, 30 page(s).

* cited by examiner

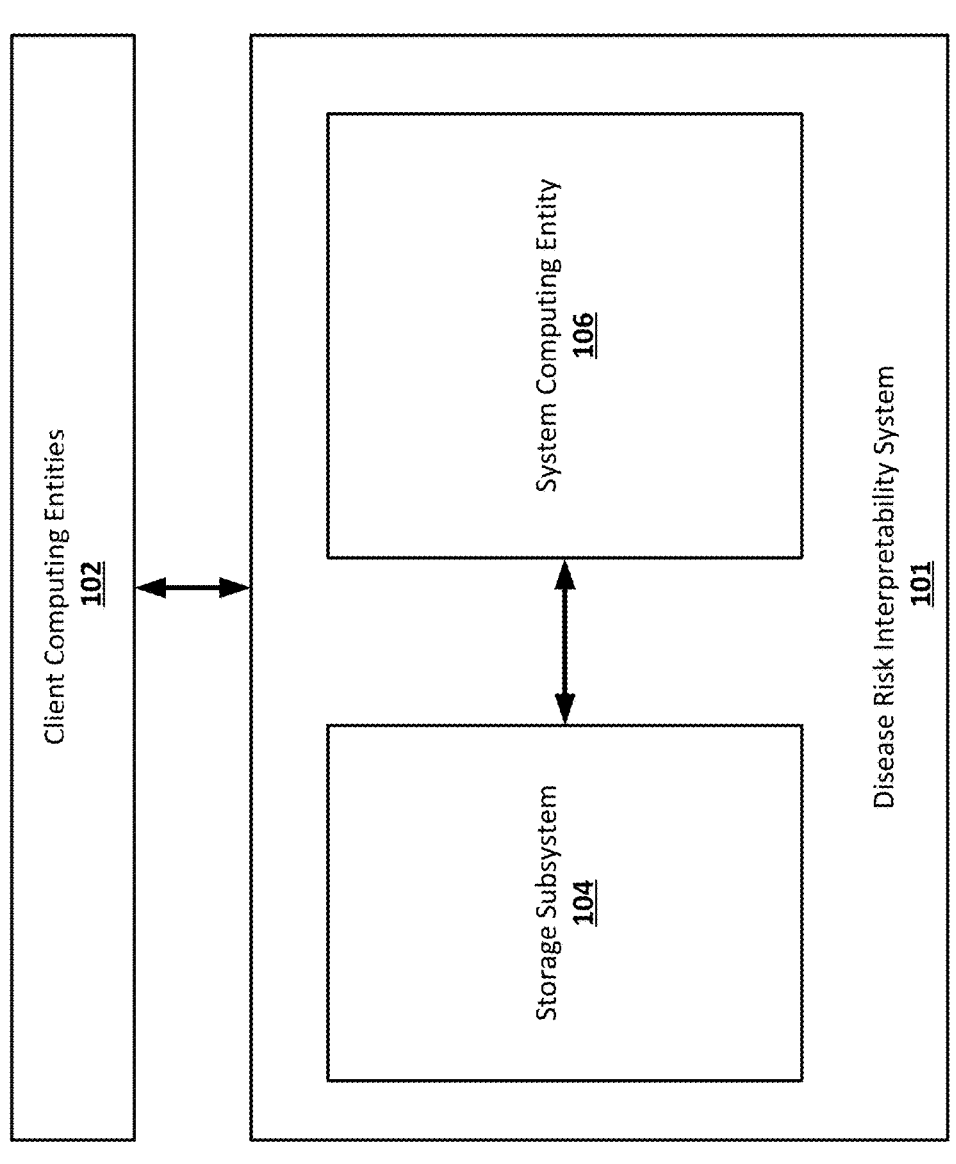
FIG. 1

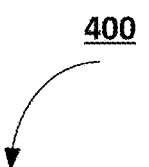

400

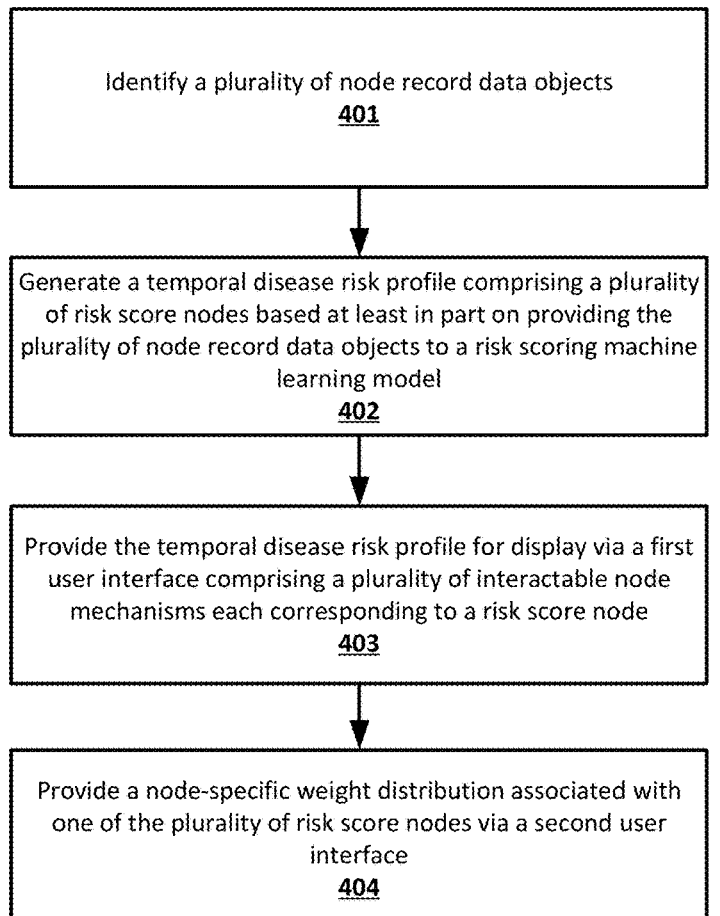

Identify a plurality of node record data objects
401

Generate a temporal disease risk profile comprising a plurality
of risk score nodes based at least in part on providing the
plurality of node record data objects to a risk scoring machine
learning model
402

Provide the temporal disease risk profile for display via a first
user interface comprising a plurality of interactable node
mechanisms each corresponding to a risk score node
403

Provide a node-specific weight distribution associated with
one of the plurality of risk score nodes via a second user
interface
404

FIG. 4

INTERACTABLE AND INTERPRETABLE TEMPORAL DISEASE RISK PROFILES

BACKGROUND

Various embodiments of the present disclosure address technical challenges related to providing interpretable temporal disease risk data and contextual information related to such data.

BRIEF SUMMARY

In general, embodiments of the present disclosure provide methods, apparatus, systems, computing devices, computing entities, and/or the like for providing interpretable and contextual temporal disease risk data. Various embodiments generate and provide for display a temporal disease risk profile, which describes a disease risk over time for a particular disease for a particular individual. Disease risk may specifically refer to a likelihood that the particular individual will be diagnosed with the particular disease at some point in the future, a likelihood that the particular individual will be symptomatic with the particular disease at some point in the future, a likelihood of full disease onset in the particular individual at some point in the future, and/or the like. Thus, via a temporal disease risk profile provided for display, one may examine and analyze progression of the particular individual's health over time in relation to the disease. Various embodiments provide temporal disease risk profiles in a dynamically interpretable manner, in which additional and/or contextual information regarding disease risk is further provided. In particular, additional information including node-specific weight distributions are provided, which describe how various individual health indicators contribute and impact the disease risk of the particular individual.

In accordance with one aspect, a computer-implemented method is provided. The method includes identifying a plurality of node record data objects. Each node record data object includes one or more sub-nodal features. The method further includes generating, based at least in part on the plurality of node record data objects and using a risk scoring machine learning model, a temporal disease risk profile comprising a plurality of risk score nodes. Each risk score node includes a risk score and a timepoint. The method further includes providing the temporal disease risk profile for display via a first user interface including a plurality of interactable node mechanisms each corresponding to a risk score node. The method further includes providing a node-specific weight distribution for display via a second user interface, the node-specific weight distribution comprising one or more sub-nodal weight values each corresponding to a sub-nodal feature of one of the plurality of node record data objects.

In accordance with another aspect, a computer program product is provided. The computer program product may include at least one computer-readable storage medium having computer-readable program code portions stored therein, the computer-readable program code portions including executable portions configured to cause at least one processor to identify a plurality of node record data objects. Each node record data object includes one or more sub-nodal features. The computer-readable program code portions include executable portions further configured to cause at least one processor to generate, based at least in part on the plurality of node record data objects and using a risk scoring machine learning model, a temporal disease risk profile including a plurality of risk score nodes. Each risk score node includes a risk score and a timepoint. The computer-readable program code portions include executable portions further configured to cause at least one processor to provide the temporal disease risk profile for display via a first user interface including a plurality of interactable node mechanism each corresponding to a risk score node. The computer-readable program code portions include executable portions further configured to cause at least one processor to provide a node-specific weight distribution for display via a second user interface. The node-specific weight distribution includes one or more sub-nodal weight values each corresponding to a sub-nodal feature of one of the plurality of node record data objects.

In accordance with yet another aspect, an apparatus including a processor and at least one memory including computer program code is provided. In various embodiments, the at least one memory and the computer program code are configured to, with the processor, cause the apparatus to identify a plurality of node record data objects. Each node record data object includes one or more sub-nodal features. The at least one memory and the computer program code are further configured to, with the processor, cause the apparatus to generate, based at least in part on the plurality of node record data objects and using a risk scoring machine learning model, a temporal disease risk profile including a plurality of risk score nodes. Each risk score node includes a risk score and a timepoint. The at least one memory and the computer program code are further configured to, with the processor, cause the apparatus to provide the temporal disease risk profile for display via a first user interface including a plurality of interactable node mechanisms each corresponding to a risk score node. The at least one memory and the computer program code are further configured to, with the processor, cause the apparatus to provide a node-specific weight distribution for display via a second user interface. The node-specific weight distribution includes one or more sub-nodal weight values each corresponding to a sub-nodal feature of one of the plurality of node record data objects.

BRIEF DESCRIPTION OF THE DRAWINGS

Having thus described the invention in general terms, reference will now be made to the accompanying drawings, which are not necessarily drawn to scale.

FIG. 1 provides an exemplary overview of an architecture that may be used to practice embodiments of the present disclosure.

Figure 2:
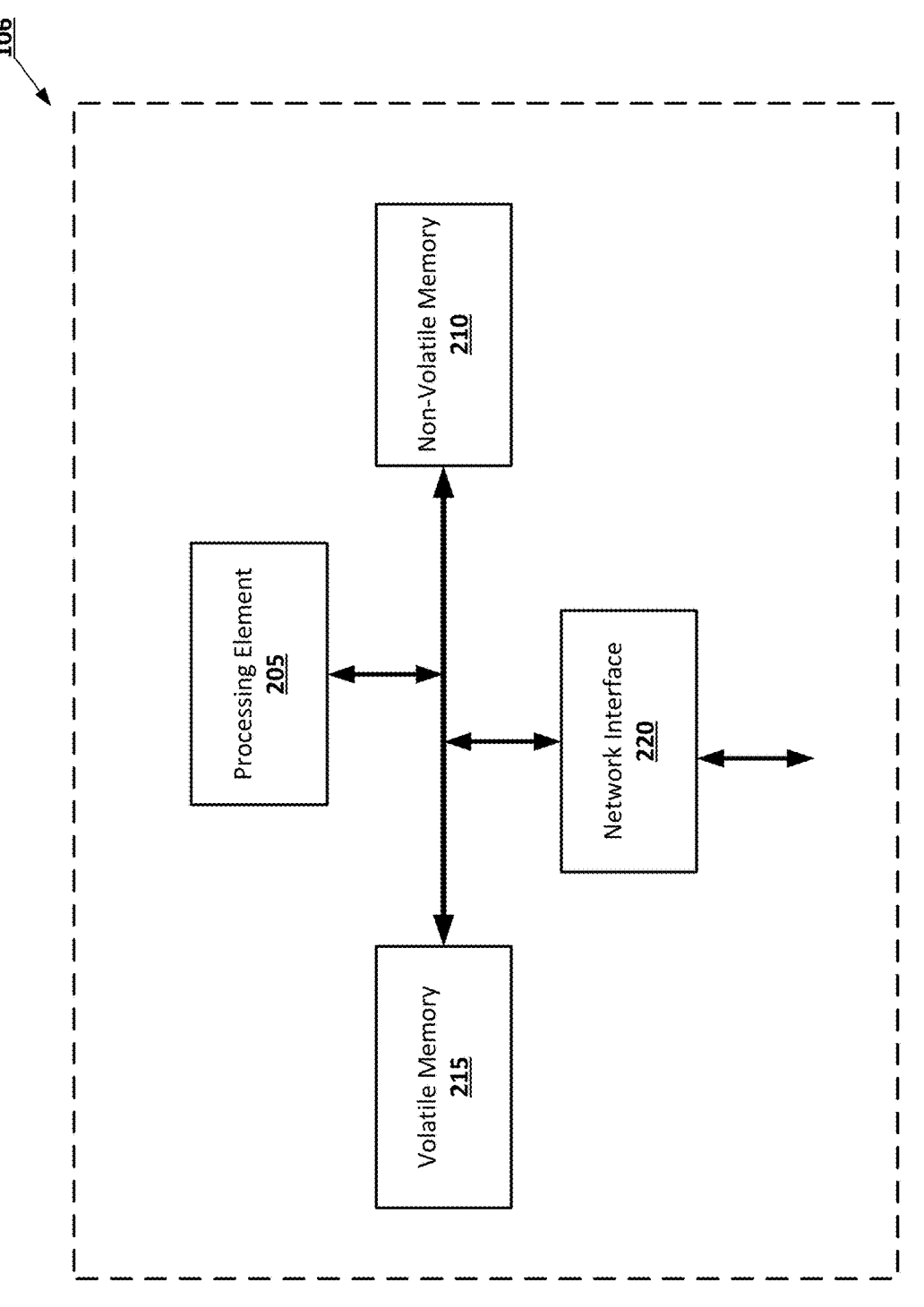

FIG. 2 provides a diagram of an example system computing entity, in accordance with some embodiments discussed herein.

Figure 3:
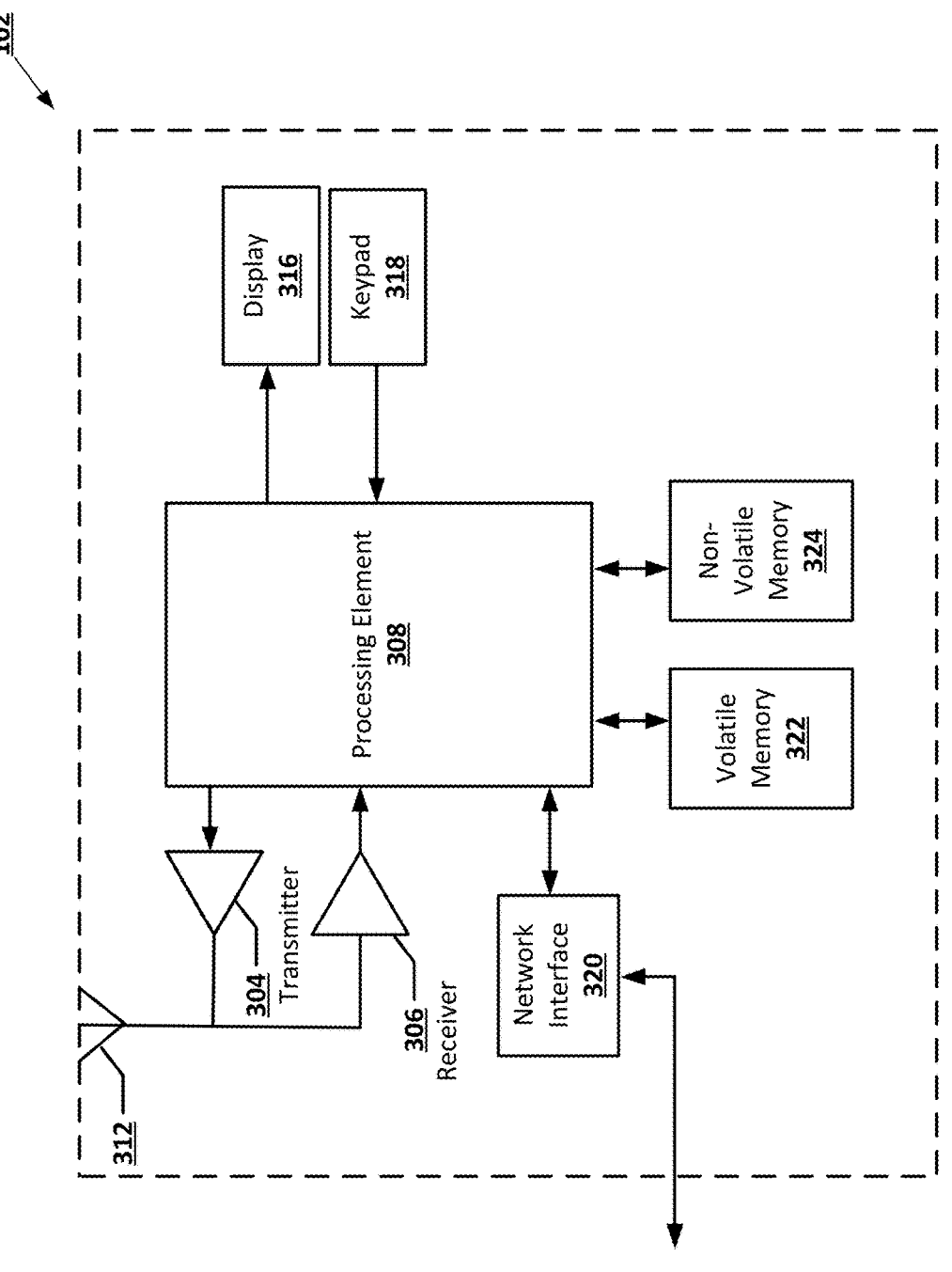

FIG. 3 provides a diagram of an example client computing entity, in accordance with some embodiments discussed herein.

FIG. 4 provides a flowchart diagram of an example process for generating and providing a temporal disease risk profile in an interpretable manner, in accordance with some embodiments discussed herein.

Figure 5:
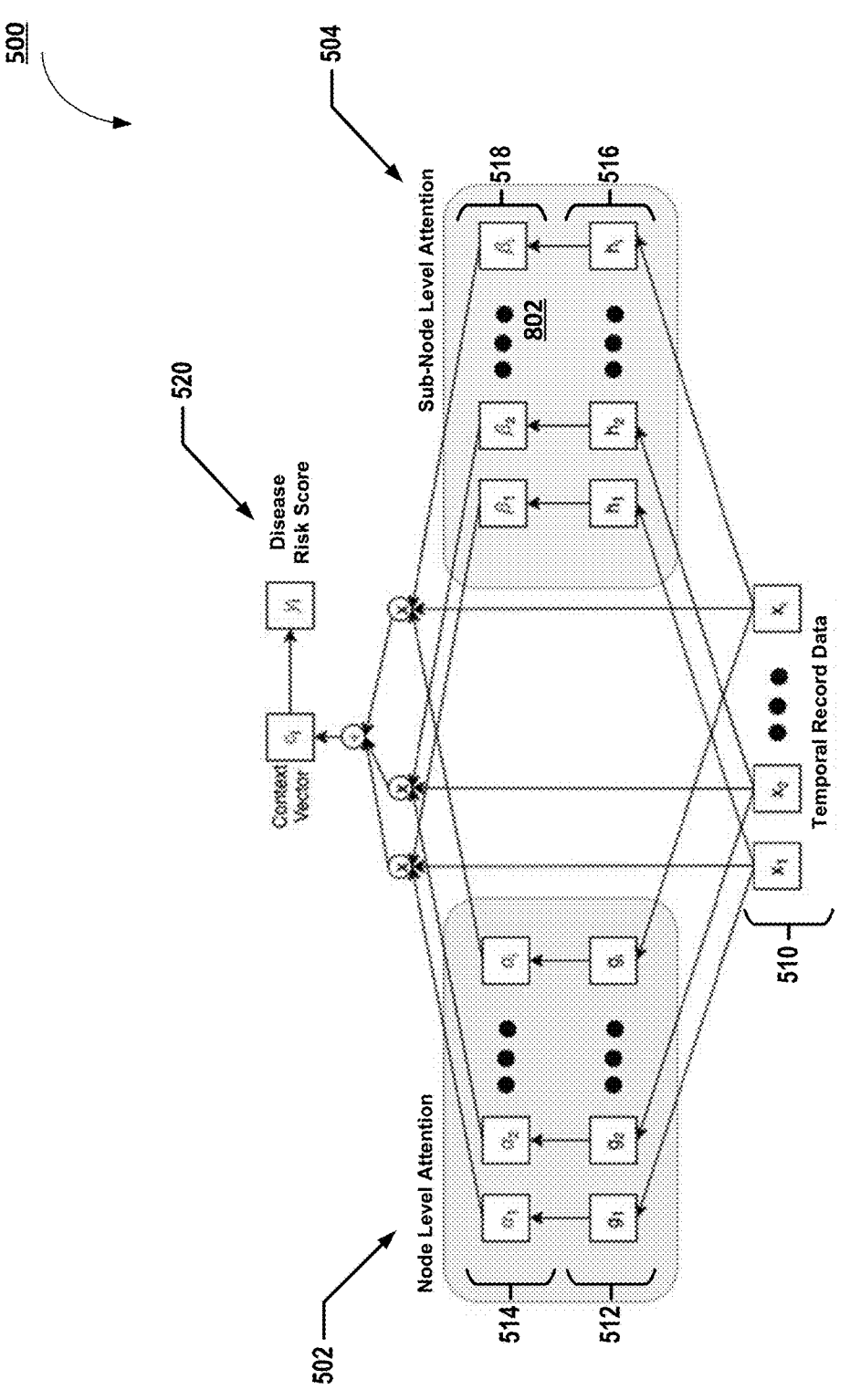

FIG. 5 provides an example risk scoring machine learning model used to generate a temporal disease risk profile, in accordance with some embodiments discussed herein.

Figure 6A:
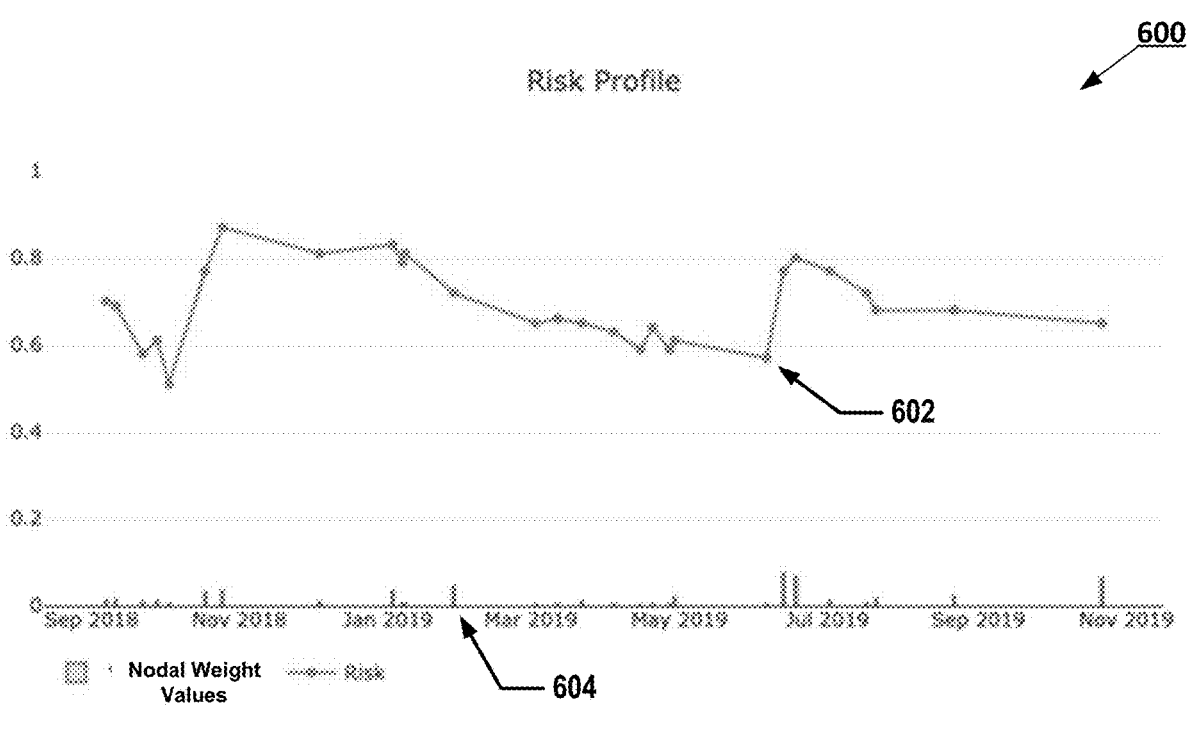
Figure 6B:
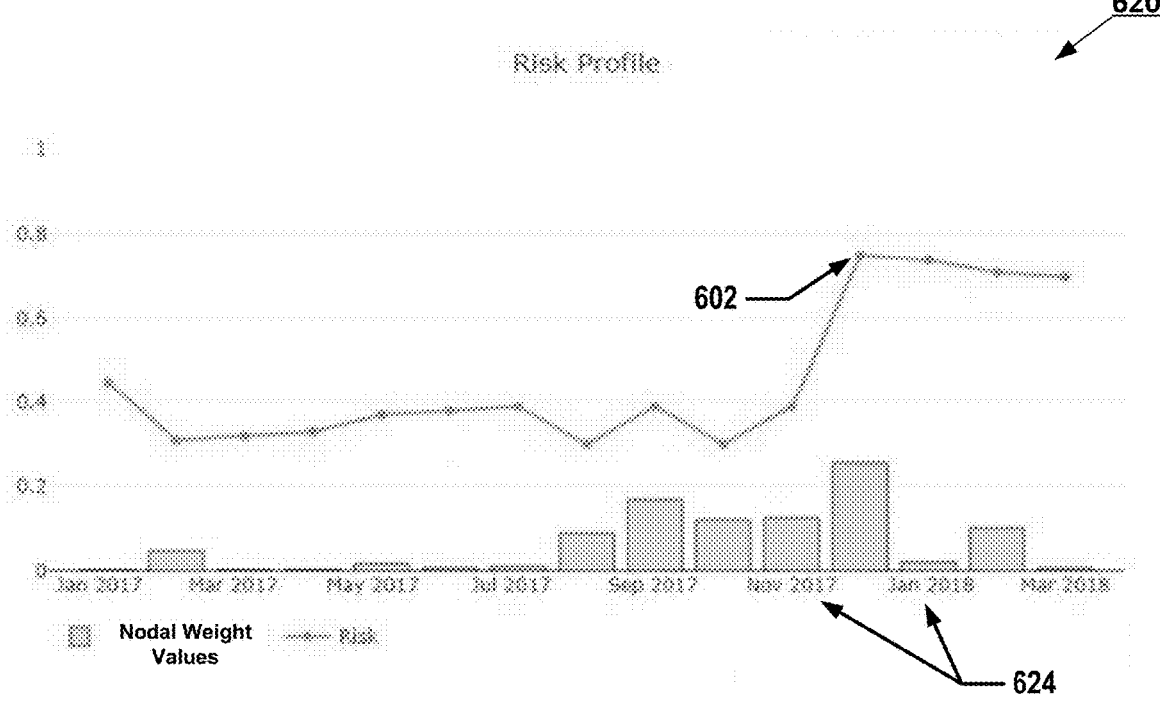

FIG. 6A and FIG. 6B each illustrate an example temporal disease risk profile, in accordance with some embodiments discussed herein.

Figure 7:
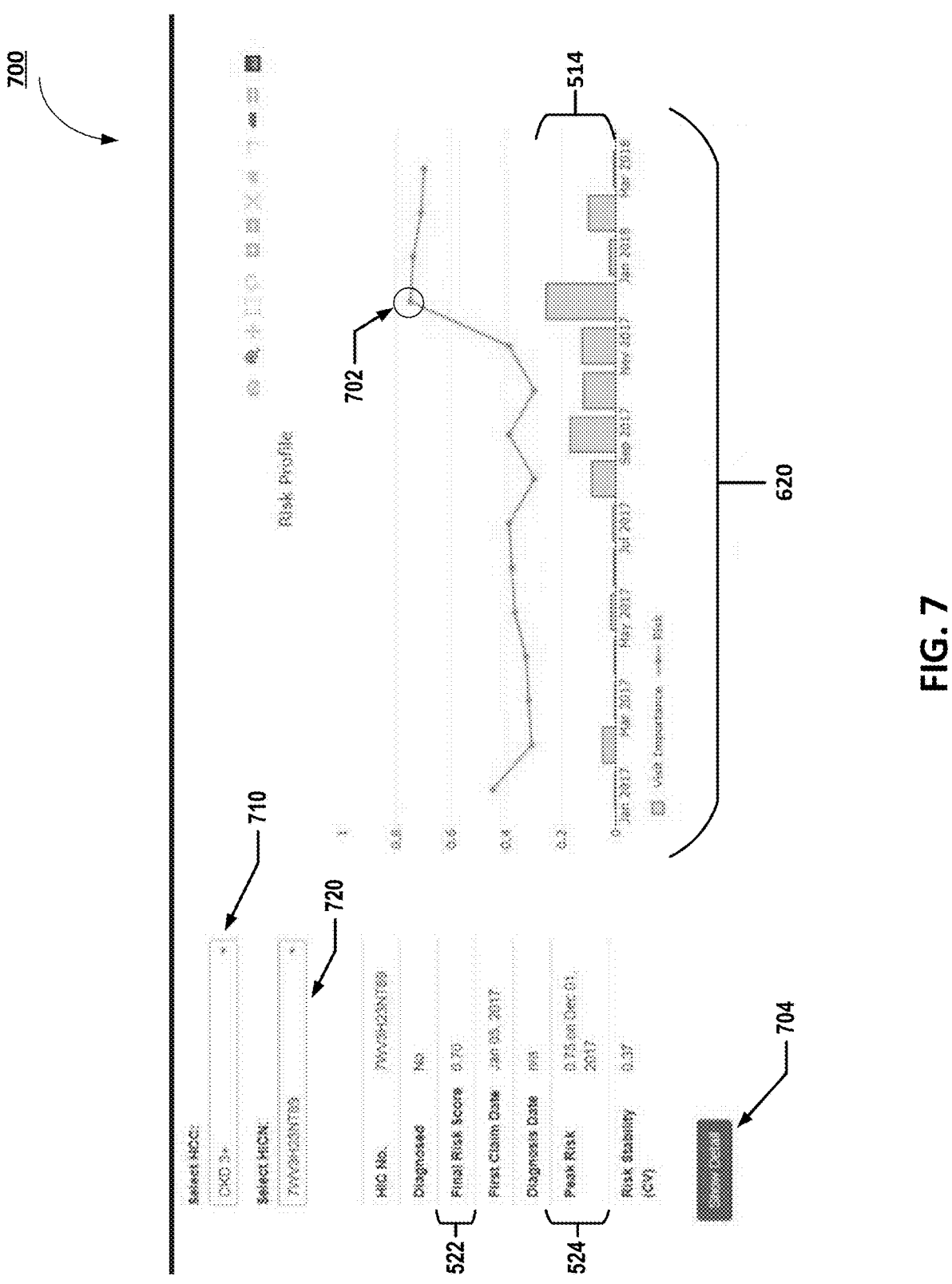

FIG. 7 provides an example user interface for providing a temporal disease risk profile for display, in accordance with some embodiments discussed herein.

Figure 8:
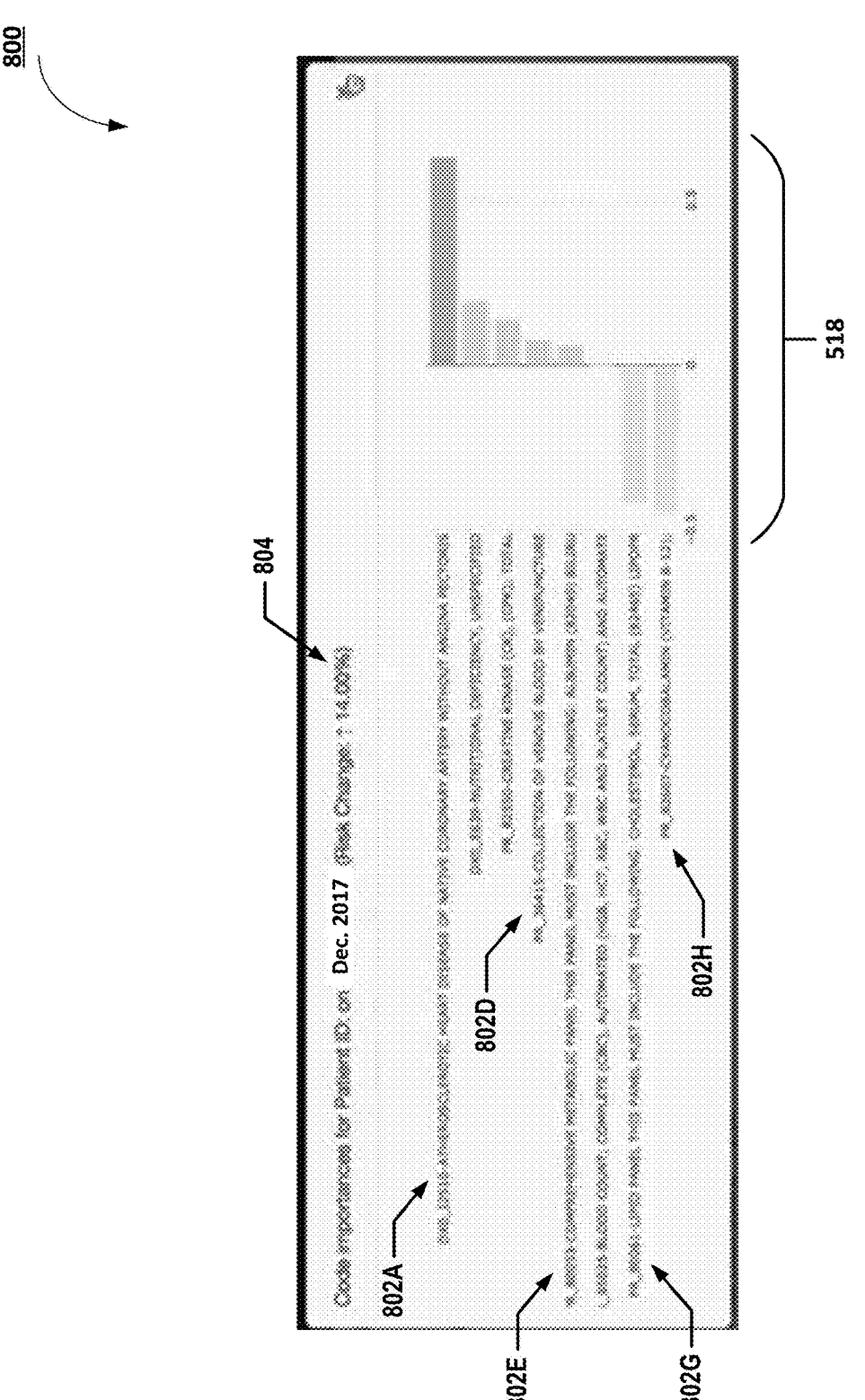

FIG. 8 provides an example interpretability layer user interface for providing interpretability information relating to a temporal disease risk profile for display, in accordance with some embodiments discussed herein.

Figure 9:
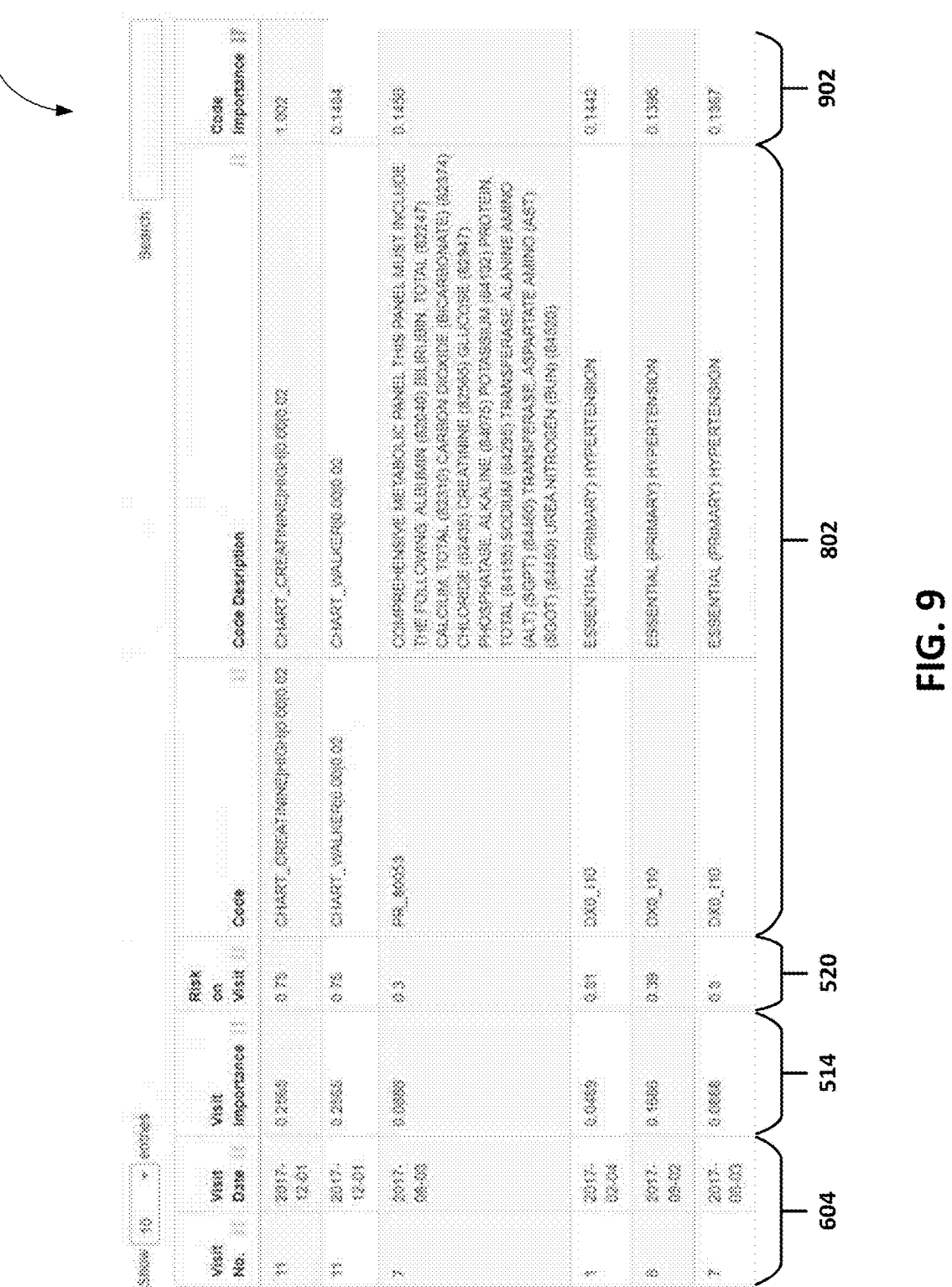

FIG. 9 provides example interpretability information relating to a temporal disease risk profile that may be provided for display, in accordance with some embodiments discussed herein.

Figure 10:
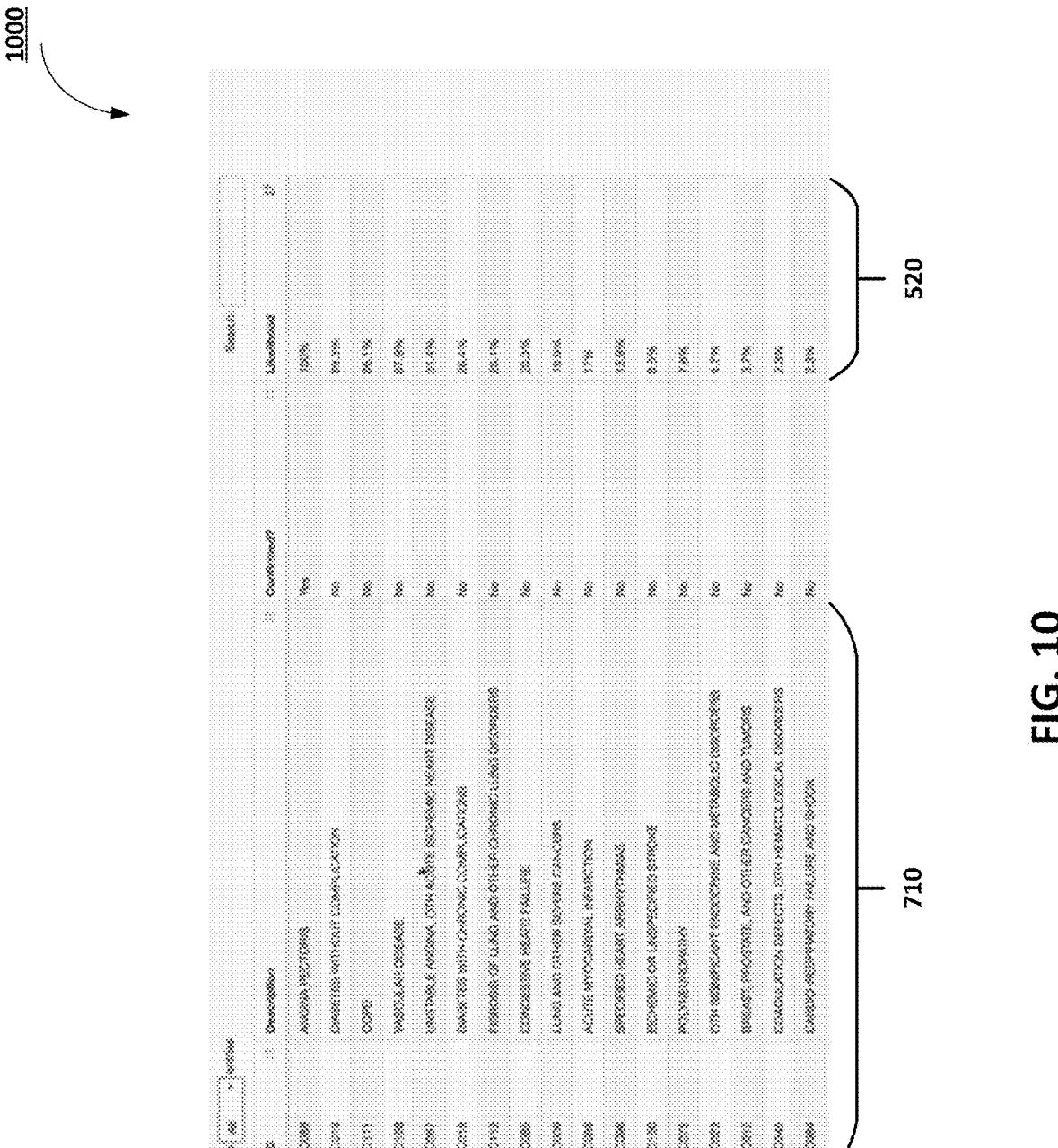

FIG. 10 provides another example interpretability layer user interface for providing interpretability information relating to an individual for display, in accordance with some embodiments discussed herein.

DETAILED DESCRIPTION

Various embodiments of the present disclosure now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present disclosure are described with reference to providing text-based summarizations of conversations, one of ordinary skill in the art will recognize that the disclosed concepts can be used in other summarization and/or text extraction applications.

I. OVERVIEW AND TECHNICAL IMPROVEMENTS

Various embodiments of the present disclosure address technical challenges related to generating and providing a temporal disease risk profile describing a likelihood of disease onset over time for an individual in a dynamically interpretable manner. A temporal disease risk profile comprises a plurality of risk score nodes each associated with a disease risk score and a timepoint and is intelligently and accurately generated using a risk scoring machine learning model. In generating risk scores for a temporal disease risk profiles, the risk scoring machine learning model weights several various health indicators or factors that are recorded for the individual over time. In example embodiments, such factors are recorded in healthcare claims data as diagnosis codes, procedure codes, pharmacy codes, and/or the like, and each factor may be weighted for generation of a risk score. That is, each factor may contribute to or may impact a risk score differently. In various embodiments, the temporal disease risk profile is provided for display via a user interface, and contributions and impacts of different factors are further provided for display for interpretability and contextual understanding of the temporal disease risk profile.

Accordingly, various embodiments of the present disclosure provide various technical advantages in providing interpretable temporal disease risk data. Various embodiments facilitate an individual-specific contextual understanding of the correlations of health factors with disease risk and of what is driving disease risk in a particular individual. Further, disease risk data is provided in a temporal manner enabling trends and patterns to be identified and further remedial, preventative, and/or the like actions to be taken. In particular, various embodiments provide comprehensive and informative temporal disease risk data efficiently, compactly, and dynamically for ease of understanding. For example, in various embodiments, a temporal disease risk profile is provided for display, and upon specific user interactions, additional interpretability information including factor weights (e.g., contribution or impact of each health factor) are also provided, thereby avoiding overload or cluttering of information. Thus, with various embodiments, one may efficiently, quickly, and comprehensively consume temporal disease risk data for an individual.

II. EXEMPLARY DEFINITIONS OF CERTAIN TERMS

The term "temporal disease risk profile" may refer to a data entity configured to describe a risk or likelihood of symptomatic onset of a particular disease over time for a particular individual. Specifically, a temporal disease risk profile is composed of disease risk scores each describing a likelihood at a corresponding timepoint of the particular individual being diagnosed at some future time with the particular disease, a likelihood of the particular individual becoming symptomatic for the particular disease, a likelihood of predicted full onset of the particular disease for the particular individual, and/or the like. Such likelihoods and the like may be generally referred herein as disease risk. A temporal disease risk profile comprises a plurality of risk score nodes each associated with a disease risk score. Each node is further associated with an event bin (e.g., a healthcare event, clinical visit) or a time bin (e.g., a periodic discretization of time). That is, a temporal disease risk profile may be event-based, with a plurality of risk score nodes describing disease risk at each healthcare event, or may be time-based, with a plurality of risk score nodes describing disease risk at each time bin. In one example embodiment, for example, a time bin is defined by a month, and a time-based temporal disease risk profile comprises a plurality of risk score nodes each describing disease risk of the individual at a corresponding month. Meanwhile, for example, an event-based temporal disease risk profile comprises a plurality of risk score nodes each describing disease risk of the individual at each recorded healthcare event. Various embodiments of the present disclosure are directed to providing temporal disease risk profiles (each associated with a disease) for an individual in an interpretable and contextual manner.

The term "node record data object" may refer to a data entity configured to record data related to one or more healthcare events within an event bin and/or within a time bin. Data recorded by node record data objects is used to generate a risk score for a risk score node of a temporal disease risk profile. A node record data object corresponds to a risk score node (e.g., a healthcare event, a time bin) of a temporal disease risk profile, and a plurality of node record data objects are used to generate a temporal disease risk profile. A node record data object comprises a plurality of sub-nodal features that individually and collectively contribute to the generation of a risk score. That is, the data recorded by a node record data object may define a plurality of sub-nodal features. In some embodiments, a node record data object is composed of one or more healthcare claims (e.g., provider claims, pharmacy claims) each comprising a plurality of codes that are defined as the sub-nodal features. For example, diagnosis codes (e.g., ICD-10), procedures codes (e.g., CPT, HCPCS), and pharmacy codes from various healthcare claims are defined as sub-nodal features and used to generate a risk score for a corresponding healthcare event or a corresponding time bin. In some instances involving time-based temporal disease risk profiles, a lack of information (e.g., a lack of healthcare claims) for a particular time bin may be indicated via a unique node record data object and/or may be indicated via a node record data object comprising a unique sub-nodal feature.

The term "risk scoring machine learning model" may refer to a data entity configured to generate disease risk scores. In various embodiments, the risk scoring machine learning model specifically uses sub-nodal features from a plurality of node record data objects to generate a plurality of disease risk scores. The risk scoring machine learning model may be configured to dynamically generate a disease risk score based at least in part on an existing plurality of node record data objects and a new node record data object, thereby enabling risk score nodes to be appended to an existing temporal disease risk profile. In various embodiments, the risk scoring machine learning model is a deep learning model comprising a long short-term memory (LSTM) mechanism and at least two attention mechanism. A first attention mechanism is configured for weighting each of a plurality of node record data objects, while a second attention mechanism is configured for weighting each sub-nodal feature within a node record data object. Accordingly, the risk scoring machine learning model is configured to capture interactions and relationships on a sub-nodal level (e.g., between sub-nodal features) and on a nodal level (e.g., between node record data objects) in the process of generating disease risk scores. In various embodiments, the risk scoring machine learning model is configured to generate multi-disease risk scores, which describe the risk or likelihood of the individual developing a particular co-morbidity, or combination of diseases. In various embodiments, term frequency-inverse document frequency (TF-IDF) techniques and/or other similar techniques are used to configure the risk scoring machine learning model (and various weights and parameters thereof) to generate disease risk scores and multi-disease risk scores.

The term "nodal weight value" may refer to a data entity configured to describe the weight of a node record data object/when generating a disease risk score. As mentioned, a plurality of node record data objects are used when generating a disease risk score, and each node record data object is associated with a nodal weight value related to the generation of the disease risk score. The nodal weight value for a node record data object and a risk score node may be considered an inferred predictive significance of the risk score node to the disease risk score and may be related to a weight specific to the node record data object within the first attention mechanism of the risk scoring machine learning model.

The term "sub-nodal weight value" may refer to a data entity configured to describe the weight of a sub-nodal feature relative to other sub-nodal features within a particular node record data object. Each sub-nodal feature contributes to the generation of a disease risk score, and each sub-nodal feature is associated with a sub-nodal weight value. The sub-nodal weight value for a sub-nodal feature may be considered an inferred predictive significance or contribution of the sub-nodal feature to the disease risk score and may be related to a weight specific to the sub-nodal feature within the second attention mechanism of the risk scoring machine learning model. A sub-nodal weight value can describe a positive contribution of a sub-nodal feature to the disease risk score (e.g., the sub-nodal feature increases disease risk) or a negative contribution of the sub-nodal feature to the disease risk score (e.g., the sub-nodal feature decreases disease risk).

The term "interactable node mechanism" may describe a data entity configured to cause interpretable information specific to a risk score node of a temporal disease risk profile to be provided. An interactable node mechanism corresponds to a risk score node, and a user interface via which a temporal disease risk profile is provided comprises a plurality of interactable node mechanisms. In various embodiments, an interactable node mechanism causes interpretable information to be provided responsive to user interaction with the interactable node mechanism. The provided interpretable information may be provided via another user interface different from the user interface within which the interactable node mechanism is positioned, in some embodiments. The provided interpretable information may specifically include a node-specific weight distribution.

The term "node-specific weight distribution" may describe a data entity configured to describe one or more sub-nodal weight values for a specific risk score node. Each risk score node is associated with a disease risk score generated using some number of sub-nodal features, and the node-specific weight distribution for a risk score node comprises sub-nodal weight values for the number of sub-nodal weight values. Thus, the node-specific weight distribution for different risk score nodes may include a different number of sub-nodal weight values.

The term "multi-level weight table" may refer to a data entity configured to, for each of a plurality of sub-nodal features, describe a corresponding sub-nodal weight value, identify a node record data object comprising the sub-nodal feature, and describe a nodal weight value of the node record data object. The multi-level weight table may be provided in any format, such as a chart, a data structure, a table, and/or the like. The multi-level weight table may be provided for display via a multi-level interpretability mechanism.

The term "multi-level interpretability mechanism" may refer to a data entity configured to cause interpretable information of a temporal disease risk profile on a sub-nodal level and a nodal level to be provided. A multi-level interpretability mechanism is positioned within a user interface and is configured to, responsive to user interaction, provide the multi-level weight table for display.

III. COMPUTER PROGRAM PRODUCTS, METHODS, AND COMPUTING ENTITIES

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example system architecture 100 for generating and providing temporal disease risk profiles for display in a dynamically interpretable manner. For example, the system architecture 100 may be used to generate a temporal disease risk profile using a risk scoring machine learning model and a plurality of node record data objects and to provide various user interfaces for displaying the temporal disease risk profile and additional interpretability information. The system architecture 100 includes a disease risk interpretability system 101 configured to generate temporal disease risk profiles and interpretability information for the temporal disease risk profiles and provide the temporal disease risk profiles and interpretability information for display. In some embodiments, the disease risk interpretability system 101 generates temporal disease risk profiles and/or user interfaces and provides the same to client computing entities 102 for display. The disease risk interpretability system 101 comprises a system computing entity 106 that may additionally or alternatively display user interfaces for the temporal disease risk profiles and interpretability information. The system computing entity 106 may be configured to generate and provide temporal disease risk profiles for display.

The disease risk interpretability system 101 further comprises a storage subsystem 104 for storing one or more risk scoring machine learning models, node record data objects used for generating temporal disease risk profiles, and/or other data used for generating and providing temporal disease risk profiles for display. The storage subsystem 104 may include one or more storage units, such as multiple distributed storage units that are connected through a computer network. Each storage unit in the storage subsystem 104 may store at least one of one or more data assets and/or one or more data about the computed properties of one or more data assets. Moreover, each storage unit in the storage subsystem 104 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

In some embodiments, the disease risk interpretability system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like). In various embodiments, the system computing entity 106 receives new node record data objects describing new health factors for an individual from a client computing entity 102, updates a temporal disease risk profile, and provides the updated temporal disease risk profile for display via an updated user interface. In various embodiments, a client computing entity 102 provides node record data objects to the system computing entity 106 via an API request, query, call, and/or the like, and the system computing entity 106 responds with an API response with a temporal disease risk profile, an updated temporal disease risk profile, and/or user interfaces.

Exemplary Computing Entities

In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

FIG. 2 provides a schematic of a system computing entity 106, according to one embodiment of the present disclosure. As shown in FIG. 2, in one embodiment, the system computing entity 106 may include, or be in communication with, one or more processing elements 205 (also referred to as processors, processing circuitry, and/or similar terms used herein interchangeably) that communicate with other elements within the system computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the system computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media 210 may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the system computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media 215 may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the system computing entity 106 with the assistance of the processing element 205 and operating system.

As indicated, in one embodiment, the system computing entity 106 may also include one or more network interfaces 220 for communicating with various computing entities (e.g., one or more other system computing entities 106, one or more client computing entities 102), such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the system computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the system computing entity 106 may include, or be in communication with, one or more input elements, such as a keyboard input, a mouse input, a touch screen/display input, motion input, movement input, audio input, pointing device input, joystick input, keypad input, and/or the like. The system computing entity 106 may also include, or be in communication with, one or more output elements (not shown), such as audio output, video output, screen/display output, motion output, movement output, and/or the like.

FIG. 3 provides a schematic of an example client computing entity 102 that may be used in conjunction with embodiments of the present disclosure. Client computing entities 102 can be operated by various parties, and the system architecture 100 may include one or more client computing entities 102. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the system computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the system computing entity 106 via a network interface 320.

Via these communication standards and protocols, the client computing entity 102 can communicate with various other entities (e.g., system computing entities 106, storage subsystem 104) using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the system computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the system computing entity 106, various other computing entities, and/or a storage subsystem 104.

In another embodiment, the client computing entity 102 may include one or more components or functionality that are the same or similar to those of the system computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

Various embodiments of the present disclosure address technical challenges related to generating and providing a temporal disease risk profile describing a likelihood of disease onset over time for an individual in a dynamically interpretable manner. A temporal disease risk profile comprises a plurality of risk score nodes each associated with a disease risk score and a timepoint and is intelligently and accurately generated using a risk scoring machine learning model. In generating risk scores for a temporal disease risk profiles, the risk scoring machine learning model weights several sub-nodal features of a plurality of node record data objects and weights the node record data objects themselves. In various embodiments, the temporal disease risk profile is provided for display via a user interface, and sub-nodal weight values and distributions thereof are further provided for display for interpretability and contextual understanding of the temporal disease risk profile.

FIG. 4 provides a flowchart diagram of an example process 400 for generating and providing a temporal disease risk profile in a dynamically interpretable manner. In various embodiments, the system computing entity 106 comprises means, such as the processor 205, memories 210, 215, network interface 220, and/or the like, for generating and providing a temporal disease risk profile (e.g., via performing steps/operations of process 400).

Process 400 comprises step/operation 401, in which a plurality of node record data objects are identified. Each of the node record data objects are associated with a particular individual. The plurality of node record data objects may be stored and retrieved from memory (e.g., storage subsystem 104, memories 210, 215) and/or may be received (e.g., via network interface 220) from one or more client computing entities 102. [Specifically discuss claim data and chart data. Each is associated with a healthcare event (no matter what binning paradigm).]]

Data recorded by node record data objects is used to generate a risk score for a risk score node of a temporal disease risk profile. A node record data object corresponds to a risk score node (e.g., a healthcare event, a time bin) of a temporal disease risk profile, and a plurality of node record data objects are used to generate a temporal disease risk profile. A node record data object comprises a plurality of sub-nodal features that individually and collectively contribute to the generation of a risk score. That is, the data recorded by a node record data object may define a plurality of sub-nodal features. In some embodiments, a node record data object is composed of one or more healthcare claims (e.g., provider claims, pharmacy claims) each comprising a plurality of codes that are defined as the sub-nodal features. For example, diagnosis codes (e.g., ICD-10), procedures codes (e.g., CPT, HCPCS), and pharmacy codes from various healthcare claims are defined as sub-nodal features and used to generate a risk score for a corresponding healthcare event or a corresponding time bin. In some instances involving time-based temporal disease risk profiles, a lack of information (e.g., a lack of healthcare claims) for a particular time bin may be indicated via a unique node record data object and/or may be indicated via a node record data object comprising a unique sub-nodal feature.

At step/operation 402, a temporal disease risk profile is generated. The temporal disease risk profile comprises a plurality of risk score nodes, which are each associated with a disease risk score and a timepoint. The temporal disease risk profile is generated based at least in part on providing the plurality of node record data objects to a risk scoring machine learning model. The risk scoring machine learning model is configured to generate disease risk scores based at least in part on the plurality of node record data objects, and each disease risk score of the temporal disease risk profile is generated based at least in part on providing the plurality of node record data objects to the risk scoring machine learning model.

FIG. 5 illustrates an operational example of a risk scoring machine learning model 500. As illustrated, the risk scoring machine learning model 500 is configured to, using a plurality of node record data objects 510, generate a disease risk score 520. In various embodiments, the plurality of node record data objects 510 is organized as a sequence of node record data objects 510 according to a timestamp or time point associated with each node record data object 510. Thus, the risk scoring machine learning model 500 is provided with node record data objects 510 in a sequence such that the temporal meaning and progression between node record data objects 510 can be learned and can be used in generating a disease risk score 520.

In various embodiments, the risk scoring machine learning model 500 is used to generate a disease risk score 520 for each time bin of a time-based temporal disease risk profile. In some instances, a node record data object may not exist for a particular time bin, such as for a period of time when no healthcare events occurred or recorded, and as such, the sequence of node record data objects 510 provided to the risk scoring machine learning model 500 includes a unique node record data object that indicates that there is no information available for a corresponding time bin. Thus, by incorporating such unique node record data objects indicating that no healthcare events occurred for a particular time bin, contextual information is considered when configuring the risk scoring machine learning model 500 and when generating a disease risk score 520. It may be appreciated that the absence of healthcare events for some time period may be suggestive that any symptoms or conditions experienced by the individual are not particularly severe and thus, disease risk may be lowered.

As shown in FIG. 5, the risk scoring machine learning model 500 comprises at least two attention mechanisms that are configured and are used when generating the disease risk score 520. In particular, the risk scoring machine learning model 500 comprises a node level attention mechanism 502 and a sub-node level attention mechanism 504. The node level attention mechanism 502 is used to generate nodal hidden states 512 for the sequence of node record data objects 510, and the nodal hidden states 512 are then processed to generate nodal weight values 514. Specifically, a nodal weight value 514 is generated for each node record data object 510 and may indicate a predicted significance, contribution, impact, and/or the like of a corresponding node record data object 510. Meanwhile, the sub-node level attention mechanism 504 is used to generate sub-nodal hidden states 516 for each sub-nodal feature of each node record data object 510, and the sub-nodal hidden states 516 are then processed to generate node-specific weight distributions 518 for each node record data object 510. Specifically, each node-specific weight distribution 518 is comprised of one or more sub-nodal weight values each describing a predicted significance, contribution, impact, and/or the like of a corresponding sub-nodal feature within the context of a node record data object 510 (e.g., relative to other sub-nodal features of the same node record data object 510). In various embodiments, the node level attention mechanism 502 and the sub-node level attention mechanism 504 are used substantially in parallel to appropriately weight the node record data objects 510 and weight the sub-nodal features thereof.

The node level attention mechanism 502 and the sub-node level attention mechanism 504 are configured (e.g., trained) to appropriately weight the node record data objects 510 of importance with higher nodal weight values 514 and weight important sub-nodal features with higher sub-nodal weight values. For example, a unique node record data object 510 indicating that no healthcare events occurred may be assigned with a lower nodal weight value 514 compared to a node record data object 510 describing various diagnoses made by a healthcare provider during a healthcare event. As a further example, a sub-nodal feature describing a diagnosis of an iron deficiency condition may be assigned with a higher sub-nodal weight value compared to a sub-nodal feature that is a procedure code describing a vision test. In particular, the node level attention mechanism 502 and/or the sub-node level attention mechanism 504 are configured in the context of a particular disease, such that sub-nodal features describing key symptoms, procedures, health conditions, and/or the like specific to the particular disease may be weighted differently than sub-nodal features describing symptoms, procedures, health conditions, and/or the like that are relatively unrelated or irrelevant to the particular disease.

Thus, the risk scoring machine learning model 500 is configured and used to generate disease risk scores 520 for a temporal disease risk profile. As mentioned, the risk scoring machine learning model 500 is configured and used to generate a disease risk score 520 for each event bin of an event-based temporal disease risk profile and/or a disease risk score 520 for each time bin of a time-based temporal disease risk profile. Referring now to FIGS. 6A and 6B, an example of an event-based temporal disease risk profile 600 is illustrated in FIG. 6A, and an example of a time-based temporal disease risk profile 620 is illustrated in FIG. 6B. The event-based temporal disease risk profile 600 is comprised of a plurality of risk score nodes 602 each comprising a disease risk score 520 for a corresponding healthcare event 604, and each healthcare event 604 is associated with a particular day. Meanwhile, the time-based temporal disease risk profile 620 is comprised of a plurality of risk score nodes 602 each comprising a disease risk score 520 for a corresponding time bin 624. It may be appreciated that a difference in time between each risk score node 602 in an event-based temporal disease risk profile 600 is not uniform, while risk score nodes 602 in a time-based temporal disease risk profile 620 are uniformly spaced with respect to time.

Returning to FIG. 4, step/operation 403 comprises providing the temporal disease risk profile for display via a first user interface. The first user interface further comprises a plurality of interactable node mechanisms each corresponding to a risk score node of the temporal disease risk profile. In various embodiments, the first user interface is displayed via the system computing entity 106. In various embodiments, the first user interface is transmitted to a client computing entity 102 and provided via a display 316 of the client computing entity 102.

FIG. 7 provides an example of a first user interface 700 for providing the temporal disease risk profile and comprising a plurality of interactable node mechanisms 702. In the illustrated embodiment, the first user interface 700 provides a time-based temporal disease risk profile 620. In the illustrated embodiment, the plurality of interactable node mechanisms 702 are co-located, positioned at, overlaid, embedded with, and/or the like the risk score nodes 602 of the temporal disease risk profile. Specifically, the temporal disease risk profile is provided in the form of a graph in which the horizontal axis describes time while the vertical axis describes disease risk score 520. Because each disease risk score describes a likelihood or probability of future disease onset, the vertical axis in the illustrated embodiment extends from 0 to 1. The first user interface 700 is further configured to indicate the disease 710 relevant to the temporal disease risk profile (e.g., the disease for which the temporal disease risk profile describes risk) as well as the individual 720 and/or an identifier for the individual. The first user interface 700 may enable selection of various diseases 710 and may be configured to display multiple temporal disease risk profiles for multiple disease 710 simultaneously (e.g., overlaid one another). As further indicated in the illustrated embodiment, the first user interface 700 is configured to indicate the final risk score 522 or most recent risk score, which may be understood as being most indicative of the disease risk for the individual 720 at the present moment in time. The first user interface 700 is also configured to indicate the peak risk score 524, or the highest disease risk score 520 described by the temporal disease risk profile, as well as an associated timestamp and/or time bin.

Returning to FIG. 4, step/operation 404 comprises providing a node-specific weight distribution 518 associated with one of the plurality of risk score nodes 602 via a second user interface. In various embodiments, step/operation 404 is performed based at least in part on user interaction with an interactable node mechanism 702 of the first user interface 700.

Each interactable node mechanism 702 is configured to cause interpretable information specific to a corresponding risk score node 602 of a temporal disease risk profile to be provided. In various embodiments, an interactable node mechanism 702 causes interpretable information to be provided responsive to user interaction (e.g., clicking, type a command, touching via a touch screen display, and/or the like) with the interactable node mechanism 702. The provided interpretable information may be provided via another user interface different from the first user interface 700 within which the interactable node mechanism is positioned, in some embodiments. Specifically, interpretable information is provided responsive to user interaction with an interactable node mechanism 702 via an interpretability layer user interface.

FIG. 8 illustrates an example of an interpretability layer user interface 800 via which interpretable information may be provided responsive to user interaction with an interactable node mechanism 702. As discussed in the context of step/operation 404, the interpretable information specifically comprises a node-specific weight distribution 518. In some embodiments, the interpretability layer user interface 800 is overlaid on the first user interface 700 and may be minimized or closed to return to the first user interface 700.

As shown in the illustrated embodiment, the interpretability layer user interface 800 provides a node-specific weight distribution 518 for display, and the node-specific weight distribution 518 may be provided as a chart (e.g., a tornado chart), a table, a graph, and/or the like. The node-specific weight distribution 518 describes one or more sub-nodal weight values for a specific risk score node 602. Each risk score node 602 is associated with a disease risk score 520 generated using some number of sub-nodal features 802 that are each weighted, and the node-specific weight distribution 518 for a risk score node 602 comprises sub-nodal weight values for the number of sub-nodal features. Thus, the node-specific weight distribution for different risk score nodes 602 may include a different number of sub-nodal weight values.

In the illustrated embodiment specifically, the example node-specific weight distribution 518 is comprised of eight sub-nodal weight values for eight sub-nodal features 802A-H. The eight sub-nodal features 802A-H are associated with (e.g., stored within, extracted from) a node record data object 510 for the time bin 624 of the interactable node mechanism 702 (e.g., time bin 624 that is the month of December 2017 where the interactable node mechanism 702 interacted with is indicated with a circle in FIG. 7). The interpretability layer user interface 800 then indicates by providing the node-specific weight distribution 518 that, for example, the first sub-nodal feature 802A describing a diagnosis of atherosclerotic heart disease of native coronary artery without angina pectoris is of more relative significance in determining disease risk compared to the fourth sub-nodal feature 802D describing a performed procedure of collecting venous blood by venipuncture. As shown, various sub-nodal weight values of the node-specific weight distribution 518 may have negative values (e.g., sub-nodal weight values for the seventh sub-nodal feature 802G and the eighth sub-nodal feature 802H). A negative sub-nodal weight value indicates that the sub-nodal feature 802 detracts and is of negative significance to disease risk. For example, a sub-nodal feature 802 describing an improvement in the health condition of the individual may have a negative sub-nodal weight value to cause the overall disease risk score 520 to decrease or to increase at a slower rate.

In various embodiments, the interpretability layer user interface 800 indicates a risk score change 804. The risk score change 804 may describe and quantify a trend between the disease risk score 520 of the risk score node 602 interacted with via the interactable node mechanism 702 and the disease risk score 520 of a preceding risk score node 602. For example, in the illustrated embodiment, the interpretability layer user interface 800 indicates a risk score change 804 of a fourteen percent increase in disease risk score 520 from the previous disease risk score 520.

Thus, interpretability layer user interfaces 800 are dynamically provided, in various embodiments, and are specific to each risk score node 602 of the temporal disease risk profile. Thus, an end user may, via the first user interface 700, select any risk score node 602 and view the node-specific weight distribution for that risk score node 602 via an interpretability layer user interface 800.

Further functionality and dynamic interpretability can also be provided, in various embodiments. In particular, various embodiments involve providing a multi-level weight table for interpretability of both sub-nodal weight values and nodal weight values 514. FIG. 9 illustrates an example of a multi-level weight table 900. The multi-level weight table 900 may be dynamically provided via the first user interface 700. As shown in FIG. 7, the first user interface 700 comprises a multi-level interpretability mechanism 704 configured to cause, responsive to user interaction, the multi-level weight table 900 to be provided for display. In some embodiments, the first user interface 700 may be updated (e.g., expanded, extended) to include the multi-level weight table 900 responsive to user interaction with the multi-level interpretability mechanism 704, while in other embodiments, the multi-level weight table 900 is provided via another user interface.

The multi-level weight table 900 is configured to, for each of a plurality of sub-nodal features 802, describe a corresponding sub-nodal weight value, identify a node record data object comprising the sub-nodal feature, and describe a nodal weight value 514 of the node record data object. The multi-level weight table 900 may be provided in any format, such as a chart, a data structure, a table, and/or the like.

In the illustrated embodiment, the multi-level weight table 900 describes six different sub-nodal features 802, each of which is identified with a "Code" column and described by a "Code Description" column. For example, the first sub-nodal feature described by the multi-level weight table 900 is chart data indicating high creatinine levels in the individual 720. The multi-level weight table 900 further comprises a "Code Importance" column describing the sub-nodal weight values 902 for each sub-nodal feature 802.

The multi-level weight table 900 further includes other columns describing nodal-level information. "Visit Number" and "Visit Date" columns describe a healthcare event 604 described by a sub-nodal feature 802. For time-based temporal disease risk profiles, the multi-level weight table 900 may describe the time bin 624 that a sub-nodal feature 802 belongs to. For example, the first sub-nodal feature may instead be described as belonging to a time bin 624 of December 2017 based at least in part on when the first sub-nodal feature was recorded (e.g., in a node record data object 510). The "Visit Importance" column describes the nodal weight value 514 of the healthcare event 604 (or a time bin 624). The multi-level weight table 900 comprises yet another column describing the disease risk score 520 at the healthcare event 604 (or time bin 624). It will be understood that while one example of a multi-level weight table 900 has been provided, multi-level information including at least the sub-nodal weight values 902, nodal weight values 514, and disease risk scores 520 may be provided in any format.

In various embodiments, further interpretability data may yet be provided. FIG. 10 illustrates a multi-disease risk table 1000 which may also be provided for display. The multi-disease risk table 1000 describes a plurality of different diseases 710 for which disease risk scores 520 are determined. For example, in the illustrated embodiment, the multi-disease risk table 1000 includes sixteen diseases including angina pectoris, diabetes without complication, and polyneuropathy. The multi-disease risk table 1000 then includes a disease risk score 520 for each disease 710. The disease risk score 520 may specifically be the final risk score 522. By providing the multi-disease risk table 1000, a comprehensive and complete understanding of the health conditions of the individual 720 may be better understood.

Accordingly, various embodiments of the present disclosure provide various technical advantages in providing interpretable temporal disease risk data. Various embodiments facilitate an individual-specific contextual understanding of the correlations of health factors with disease risk and of what is driving disease risk in a particular individual. Further, disease risk data is provided in a temporal manner enabling trends and patterns to be identified and further remedial, preventative, and/or the like actions to be taken. In particular, various embodiments provide comprehensive and informative temporal disease risk data efficiently, compactly, and dynamically for ease of understanding. For example, in various embodiments, a temporal disease risk profile is provided for display, and upon specific user interactions, additional interpretability information including factor weights (e.g., contribution or impact of each health factor) are also provided, thereby avoiding overload or cluttering of information. Thus, with various embodiments, one may efficiently, quickly, and comprehensively consume temporal disease risk data for an individual.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method comprising:
providing for display, by one or more processors and via a first interactable user interface, a profile associated with a machine learned model, wherein:
(i) the first interactable user interface comprises (a) an interactive graph that comprises a horizontal axis defined by a plurality of time bins and a vertical axis defined by a plurality of model outputs from the machine learned model, (b) a plurality of interactable node mechanisms respectively corresponding to a plurality of nodes of the profile, (c) a plurality of nodal weight indications respectively corresponding to the plurality of nodes, and (d) a multi-level interpretability mechanism configured to display, upon selection, a multi-level weight table of the profile,
(ii) a node of the plurality of nodes is displayed within the interactive graph (a) at a horizontal position along the horizontal axis based at least in part on one of the plurality of time bins corresponding to the node and (b) at a vertical position of the vertical axis based on a one of the plurality of model outputs corresponding to the node,
(iii) an interactable node mechanism of the plurality of interactable node mechanisms that corresponds to the node is overlaid at the horizontal position and the vertical position, and
responsive to a selection of the interactable node mechanism that corresponds to the node via the first interactable user interface, providing for display, by the one or more processors and via a second interactable user interface, one or more feature weights and one or more sub-nodal features of the node, wherein the one or more feature weights and the one or more sub-nodal features of the node are retrieved from a data store corresponding to the machine learned model; and responsive to a selection of the multi-level interpretability mechanism, dynamically providing for display, by the one or more processors and via the first interactable user interface, the multi-level weight table configured to, for the node, provide a contextual description for (i) the one or more sub-nodal features, and (ii) the one or more feature weights.

2. The computer-implemented method of claim 1, wherein a feature weight of the one or more feature weights is one of a node-specific weight distribution.

3. The computer-implemented method of claim 1, wherein the second interactable user interface indicates a percent change from a preceding model output of a preceding node to the model output of the node.

4. The computer-implemented method of claim 1, further comprising providing a multi-disease risk table for display, the multi-disease risk table indicating one or more multi-disease risk scores, wherein the machine learning model is configured to generate a multi-disease risk score.

5. The computer-implemented method of claim 1, wherein the multi-level weight table comprises: (i) a code column that identifies a sub-nodal feature of the one or more sub-nodal features of the node, (ii) a code description column that describes the sub-nodal feature, (iii) a code importance column that describes one or more corresponding second feature weights of the sub-nodal feature, and (iv) a visit importance column that describes the first feature weight of the node.

6. A system comprising:

one or more processors; and one or more memories storing processor-executable instructions that, when executed by the one or more processors, cause the one or more processors to perform operations comprising:

providing for display, via a first interactable user interface, a profile associated with a machine learned model, wherein:

(i) the first interactable user interface comprises (a) an interactive graph that comprises a horizontal axis defined by a plurality of time bins and a vertical axis defined by a plurality of model outputs from the machine learned model, (b) a plurality of interactable node mechanisms respectively corresponding to a plurality of nodes of the profile, (c) a plurality of nodal weight indications respectively corresponding to the plurality of nodes, and (d) a multi-level interpretability mechanism configured to display, upon selection, a multi-level weight table of the profile, (ii) a node of the plurality of nodes is displayed within the interactive graph (a) at a horizontal position along the horizontal axis based at least in part on one of the plurality of time bins corresponding to the node and (b) at a vertical position of the vertical axis based on one of the plurality of model outputs corresponding to the node, (iii) an interactable node mechanism of the plurality of interactable node mechanisms that corresponds to the node is overlaid at the horizontal position and the vertical position, and responsive to a selection of the interactable node mechanism that corresponds to the node via the first interactable user interface, providing for display, via a second interactable user interface, one or more feature weights and one or more sub-nodal features of the node, wherein the one or more feature weights and the one or more sub-nodal features of the node are retrieved from a data store corresponding to the machine learned model; and responsive to a selection of the multi-level interpretability mechanism, dynamically providing for display, via the first interactable user interface, the multi-level weight table configured to, for the node, provide a contextual description for (i) the one or more sub-nodal features, and (ii) the one or more feature weights.

7. The system of claim 6, wherein a feature weight of the one or more feature weights is one of a node-specific weight distribution.

8. The system of claim 6, wherein the second interactable user interface indicates a percent change from a preceding model output of a preceding node to the model output of the node.

9. The system of claim 6, further comprising providing a multi-disease risk table for display, the multi-disease risk table indicating one or more multi-disease risk scores, wherein the machine learning model is configured to generate a multi-disease risk score.

10. One or more non-transitory computer-readable media storing processor-executable instructions that, when executed by one or more processors, cause the one or more processors to perform operations comprising:

providing for display, via a first interactable user interface, a profile associated with a machine learned model, wherein:

(i) the first interactable user interface comprises (a) an interactive graph that comprises a horizontal axis defined by a plurality of time bins and a vertical axis defined by a plurality of model outputs from the machine learned model, (b) a plurality of interactable node mechanisms respectively corresponding to a plurality of nodes of the profile, (c) a plurality of nodal weight indications respectively corresponding to the plurality of nodes, and (d) a multi-level interpretability mechanism configured to display, upon selection, a multi-level weight table of the profile, (ii) a node of the plurality of nodes is displayed within the interactive graph (a) at a horizontal position along the horizontal axis based at least in part on a time bin corresponding to the node and (b) at a vertical position of the vertical axis based on a model output corresponding to the node, (iii) an interactable node mechanism of the plurality of interactable node mechanisms that corresponds to the node is overlaid at the horizontal position and the vertical position, and responsive to a selection of the interactable node mechanism that corresponds to the node via the first interactable user interface, providing for display, via a second interactable user interface, one or more feature weights and one or more sub-nodal features of the node, wherein the one or more feature weights and the one or more sub-nodal features of the node are retrieved from a data store corresponding to the machine learned model; and responsive to a selection of the multi-level interpretability mechanism, dynamically providing for display, via the first interactable user interface, the multi-level weight table configured to, for the node, provide a contextual description for (i) the one or more sub-nodal features, and (ii) the one or more feature weights.

11. The one or more non-transitory computer-readable media of claim 10, wherein a feature weight of the one or more feature weights is one of a node-specific weight distribution.

12. The one or more non-transitory computer-readable media of claim 10, wherein the second interactable user interface indicates a percent change from a preceding model output of a preceding node to the model output of the node.

\* \* \* \* \*